United States Patent [19]

Juguin et al.

[11] 3,980,721

[45] Sept. 14, 1976

[54] CATALYST PARTICULARLY USEFUL FOR DEHYDROGENATING SATURATED HYDROCARBONS

[75] Inventors: Bernard Juguin; Jean-Francois Le Page, both of Rueil-Malmaison, France

[73] Assignee: Institut Francaise du Petrole, des Carburants et Lubrifiants et Entreprise de Recherches et d'Activites Petrolieres Elf, Rueil-Malmaison, France

[22] Filed: Apr. 3, 1975

[21] Appl. No.: 564,838

Related U.S. Application Data

[62] Division of Ser. No. 304,543, Nov. 7, 1972, Pat. No. 3,887,495.

[30] Foreign Application Priority Data

Nov. 19, 1971  France .............................. 71.41426

[52] U.S. Cl. ..................... 260/668 D; 260/666 A; 260/683.3
[51] Int. Cl.² ........................................ C07C 15/00
[58] Field of Search ............... 260/683.3, 668 D; 208/139

[56] References Cited
UNITED STATES PATENTS

| | | |
|---|---|---|
| 3,584,060 | 6/1971 | Rausch ............................ 260/683.3 |
| 3,644,559 | 2/1972 | Kobylinski et al. ............. 260/683 D |
| 3,649,564 | 3/1972 | Hayes ............................. 252/461 X |
| 3,692,863 | 9/1972 | Kmecak et al. ................ 252/465 PT |
| 3,725,246 | 4/1973 | Kmecak et al. .................. 260/683.3 |
| 3,759,841 | 9/1973 | Wilhelm ......................... 252/466 PT |
| 3,764,557 | 10/1973 | Kluksdahl .......................... 208/139 |
| 3,781,221 | 12/1973 | Kominam et al. ............. 252/464 X |

OTHER PUBLICATIONS

Balaudiu, A. A. et al., Izvest. Akad. Nauk S.S.S.R. Otdel Khim Nauk, 1959, pp. 1365–1371.
Balaudiu, A. A. et al., Redkie Metallyi Splavy, Trudy Pervogo Vsesoyuz. Soveschauiya po Splavani Redkikh Metal, Akad. Nauk, S.S.S.R. Inst. Metal, Moscow, 1957, pp. 72–79.
Balaudiu, A. A. et al., Akad. Nauk, S.S.S.R. Inst. Met., 1958, pp. 170–179.

*Primary Examiner*—Veronica O'Keefe
*Attorney, Agent, or Firm*—Millen, Raptes & White

[57] ABSTRACT

New catalyst, particularly suitable for dehydrogenating saturated hydrocarbons, which contains alumina, at least one metal selected from molybdenum, tungsten and rhenium and at least one metal selected from gallium, indium, thallium, germanium, tin, lead, antimony and bismuth, said catalyst having a specific surface from 20 to 150 m²/g and a neutralization heat by ammonia absorption at 320°C under 300 mm Hg lower than 10 calories per gram.

26 Claims, No Drawings

CATALYST PARTICULARLY USEFUL FOR DEHYDROGENATING SATURATED HYDROCARBONS

This is a division of application Ser. No. 304,543, filed Nov. 7, 1972 now U.S. Pat. No. 3,887,495.

This invention concerns a catalyst which may be used in particular for dehydrogenating hydrocarbons to the corresponding unsaturated hydrocarbons containing the same number of carbon atoms in the molecule.

A particularly interesting application of this invention consists in dehydrogenating straight chain paraffinic hydrocarbons containing from 3 to 40 carbon atoms. The products obtained from the dehydrogenation of straight chain hydrocarbons constitute in fact a remarkable raw material for the manufacture of detergent compositions of the alkylaromatic sulfonate or sulfate type which are sensitive to biological degradation.

Another interesting application of the present invention consists in separating the dehydrogenation products and subsequently coverting them to long chain alcohols by OXO synthesis.

Another application of the invention consists of dehydrogenating naphthenic hydrocarbons containing from 3 to 40 carbon atoms per molecule and particularly naphthenic hydrocarbons having 5, 6, 7 or 8 bonds; during the dehydrogenation of these hydrocarbons, the naphthenes are almost entirely converted to aromatic hydrocarbons.

It is well known that the saturated hydrocarbons may be converted to unsaturated hydrocarbons by catalytic dehydrogenation. Many processes and catalysts have been elaborated for dehydrogenating n-paraffins to the corresponding olefins. A typical example consists in the dehydrogenation of n-butane to butenes, in the presence of a catalyst consisting of chromium oxide deposited on alumina. Among the other suggested catalysts, there can be mentioned those containing noble metals such as platinum and palladium deposited on a carrier such as alumina, silica or a combination thereof. These particular catalysts when used in the known processes, have been proved to result in an excessive formation of carbon or coke which is responsible for a quick decrease of the catalyst activity. Moreover, these catalysts initiate detrimental secondary reactions, such as cracking, aromatization and isomerization of the skeleton and production of polyunsaturated hydrocarbons such as dienes and trienes. As the desired product is generally a monoethylenic hydrocarbon, these secondary reactions reduce the efficiency of the process, so that the latter as well as the used catalysts appear as having a low economical interest.

The present invention has therefore as objects:

a catalyst and a process for dehydrogenating saturated hydrocarbons, whereby the undesirable secondary reactions such as cracking, aromatization and isomerization are very substanially minimized;

a catalyst and a process for dehydrogenating saturated hydrocarbons to monoethylenic hydrocarbons, with a minimum conversion to polyethylenic hydrocarbons;

a catalyst and a process whereby the saturated hydrocarbons may be dehydrogenated with a minimum coke formation, and with the maintenance of a very high catalytic activity over a very long period.

These objects are achieved according to the invention by the use of a catalyst containing (a) alumina (b) at least one metal selected from groups VI B and VII B of the periodic classification of the elements and (c) at least ome metal selected from groups III A, IV A and V A of the periodic classification of the elements, and optionally (d) at least one metal from group VIII of the periodic classification.

The metal from groups VI B and VII B of the periodic classification is selected from the group of metals consisting of molybdenum, tungsten and rhenium.

The metal from groups III A, IV A and V A of the periodic classification of the elements is selected from the group of metals consisting of gallium, indium, thallium, germanium, tin, lead, antimony and bismuth. The metal from group VIII of the periodic classification is selected from the group of metals consisting of platinum, iridium, palladium, ruthenium and rhodium.

The catalyst used will be a substantially neutral one, i.e. a catalyst whose neutralization heat by ammonia adsorption is lower than about 10 calories per gram of catalyst at 320°C, and under a pressure of 300 mm of mercury.

The acidity of the catalyst has been determined by the known test of ammonia adsorption of the same type as that described for example in "Journal of Catalysis, 2, 211–222 (1963)": this method consists of heating the catalyst to 600°C, under vacuum (0.01 mm of mercury) up to a complete gas removal (particularly for removing the water and the undesirable impurities): subsequently the catalyst is placed in a calorimeter at 320°C, in which is introduced such an ammonia amount that the final pressure of the system attain 300 mm of mercury, and the heat evolved is measured.

The catalyst must therefore have a neutralization heat by ammonia adsorption lower than about 10 calories per gram of catalyst at 320°C under a pressure of 300 mm of mercury (the neutralization heat of alumina used as a carrier is substantially identical, i.e., lower than 10 calories per gram of catalyst). The catalyst must also have a specific surface of about 20 to 150 m²/g, preferably about 40 to 80 m²/g; the pore volume of the catalyst will be, for example, about 0.4 to 0.8 cc/g, at least 75% of the porosity corresponding to pores of an average diameter from 100 to 500 angstroms (the specific surface and the pore volume of the alumina used as a carrier are thus substantially identical to the above-mentioned values).

The aluminae which can be used as carrier are not all equivalent, and it is preferred to make use of gamma alumina balls (for example tetragonal gamma). There can however be used also other alumina conglomerates such as extrudates or pills complying with the above mentioned conditions.

When the acidity of the alumina carrier is deemed too high, it can be decreased by adding, before or after the dehydrogenation elements, certain basic compounds or compounds capable of being decomposed under the conditions of the reaction to give basic compounds; as examples of such compounds there will be mentioned the oxides and hydroxides of alkali or alkaline earth metals, as well as carbonates and other salts of weak acids (acid dissociation constant preferably lower than $10^{-3}$) of the same metals, for example sodium hydroxide, potassium hydroxide, sodium carbonate, potassium carbonate, calcium acetate, sodium nitrate or magnesium acetate. It is generally unnecessary to add more than 2 %, or even more than 1 % of basic compounds (by weight with respect to the catalyst carrier).

The total weight content, with respect to the catalyst, of the metal from groups VI B and VII B is preferably from 0.01 to 1%, more particularly from 0.1 to 0.5%, the content by weight of elements from groups III A, IV A and V A is from 0.1 to 1%, preferably from 0.1 to 0.5 %, and the content by weight of elements from group VIII, if any, is from 0.01 to 1 %, preferably from 0.1 to 0.5 %.

The dehydrogenating elements (metals from groups VI B, VII B and optionally VIII, and elements from groups III A, IV A and V A) may be deposited separately or simultaneously on the carrier by means of solutions containing the same, for example aqueous solutions of platinum, iridium, rhodium, ruthenium and palladium chlorides, hexachloroplatinic and hexachloroiridic acids, hexachloroplatinates and noble hexachlorometallates, platinum and noble metal diaminodinitrites, ammonium, sodium or potassium meta- or para- tungstate, ammonium, sodium or potassium paramolybdate, perrhenic acid, ammonium, sodium or potassium perrhenate, gallium, indium, thallium, germanium, tin, lead, antimony and bismuth nitrates, chlorides and oxalates.

After the dehydrogenating elements have been deposited on the carrier, the catalyst is then dried, roasted by heating in an oxidizing atmosphere at a temperature, for example from 300° to 600°C, then reduced in a hydrogen stream at a temperature for example from 350° to 700°C for 2 to 30 hours with a hydrogen hourly flow rate of about 100 to 1000 times the catalyst volume. This last operation is preferably conducted in the dehydrogenation reactor. It is also possible to omit the roasting step and to directly carry out the reduction.

The conditions of use of these catalysts are not equivalent. When dehydrogenating straight chain paraffinic hydrocarbons, in order to obtain reasonable conversion rates, the temperature will be from 300° to 600°C, preferably from 400° to 500°C, with hourly flow rates by volume of liquid saturated hydrocarbons from 0.1 to 30 times and advantageously from 2 to 10 times the catalyst volume; with absolute pressures of from 0.1 to 20 bars and preferably from 1 to 5 bars. The hydrogen partial pressure has a very significant influence on the stability of these catalysts; the molar ratio of the hydrogen to the hydrocarbons, at the reactor inlet, may be selected from 0.1 to 30, advantageously from 2 to 20 and preferably from 8 to 15. When dehydrogenating cyclic hydrocarbons, in order to obtain reasonable conversion rates, the temperature will be selected from 300° to 600°C, preferably from 500° to 600°C, with hourly flow rates by volume of liquid hydrocarbons from about 0.1 to 20 times the catalyst volume and advantageously from 2 to 10 times this volume and with absolute pressures of from 1 to 60 bars, preferably from 5 to 40 bars. The hydrogen partial pressure is very important for the stability of these catalysts, the molar ratio of the hydrogen to the hydrocarbons, at the inlet of the reactor, may be selected from 0.5 to 30 and advantageously from 2 to 10. As examples of hydrocarbons which may be subjected to dehydrogenation, there will be mentioned, in addition to the cuts containing hydrocarbon mixtures, propane, n-butane, isobutane, isopentane, n-hexane, n-heptane, n-dodecane, n-hexadecane, cyclopentane, cyclohexane, cycloheptane, cyclooctane and methylcyclopentane. The following non limitative examples illustrate the invention.

EXAMPLE 1

A cut of $C_{10}$- $C_{14}$ normal paraffins is contacted in a dehydrogenation reactor of steel having an internal diameter of 2cm and a length of 40 cm, with a catalyst $A_1$ based on rhenium and tin deposited on gamma alumina balls. This catalyst has been prepared by impregnation of gamma alumina balls of 69 m²/g specific surface, whose pore volume is 58 cc per 100 g (75% of this pore volume corresponding to pores having an average diameter from 100 to 500 A). The heat of neutralization by ammonia adsorption of this gamma alumina was 7 calories per gram. 100 g of this alumina balls are first impregnated with 58 cc of an aqueous solution containing 20.4 cc of a perrhenic acid solution with a 0.98 % rhenium content by weight. After impregnation and drying, 0.38 g of stannous chloride di-hydrate are added thereto, the contact being maintained for 3 hours; after 3 hours, the alumina balls have completely absorbed the solution. They are then dried in a drying oven at 100°C for 6 hours, and then roasted in an air stream for 2 hours at 400°C, then for 2 hours at 500°C. After cooling, the catalyst is transferred into a dehydrogenation reactor where it is reduced for about 12 hours at 530°C in a hydrogen stream of 50 liters/hour.

The resulting catalyst contains 0.2% by weight of rhenium and 0.2 % by weight of tin; its neutralization heat by ammonia adsorption is 7 calories per gram, its specific surface is 62 m²/g and its pore volume 54 cc/100 g.

The $C_{10}$- $C_{14}$ cut is passed over the catalyst at a spatial velocity of 2 liquid volumes per volume of catalyst and per hour, at a temperature of 470°C, an absolute pressure of 1.5 bar, and a molar ratio of the hydrogen to the $C_{10}$–$C_{14}$ cut equal to 10 at the inlet of the reactor; the liquid and gaseous products issued from the reactor have then been analyzed during time, by determination of the bromine number, by gas phase chromatography, mass spectrometry and nuclear magnetic resonance. The results are given in Table I hereinafter.

EXAMPLE 2

According to the technique of example, 1, 5 catalysts A-$A_2$- $A_3$- $A_4$ and $A_5$, whose neutralization heat by ammonia adsorption is about 7 calories per gram, having a specific surface of about 62 m²/g and a pore volume of about 54 cc/100 g, have been prepared with the respective following composition by weight:

A : 0.2 % of rhenium
$A_2$ : 0.2 % of rhenium and 0.2 % of gallium
$A_3$ : 0.2 % of rhenium and 0.2 % of germanium
$A_4$ : 0.2 % of rhenium and 0.2 % of indium
$A_5$ : 0.2 % of rhenium and 0.2 % of antimony.

The example carried out in the presence of catalyst A is given only by way of comparison and forms no part of the invention.

A $C_{10}$– $C_{14}$ cut as in example 1, is passed over this catalyst under the same operating conditions as in example 1. The results are given in table I.

Moreover, by way of comparison, the $C_{10}$– $C_{14}$ cut of example 1 has been passed, under the same operating conditions as in this example, over a conventional catalyst B, containing alumina and 0.2 % of platinum; the catalyst B has been prepared according to a method similar to that of example 1, except that the perrhenic acid has been replaced by 58 cc of an aqueous solution containing 7.7 cc of a hexachloroplatinic acid solution containing 2.6 % by weight of platinum. The catalyst B has a specific surface of 62 m²/g and a pore volume of 54 cc/100 g; its neutralization heat by ammonia adsorption is 7 calories per gram.

1, under the operating conditions mentioned in this example.

The examples carried out in the presence of catalysts

TABLE I

| Catalyst | Catalyst age in hours | Composition by weight of the liquid product | | | | | % of the feed cracked to $C_1$-$C_5$ hydrocarbons |
|---|---|---|---|---|---|---|---|
| | | n-paraffins | n-mono olefins | iso-olefins + isoparaffins | diolefins | aromatics | |
| A | 4 | 83.3 | 15.7 | 0.3 | 0.1 | 0.5 | 0.1 |
| | 50 | 85.3 | 14 | 0.2 | 0.1 | 0.3 | 0.1 |
| | 200 | 86.1 | 13.3 | 0.2 | 0.1 | 0.2 | 0.1 |
| | 400 | 87.1 | 12.5 | 0.1 | — | 0.2 | 0.1 |
| $A_1$ | 4 | 69.7 | 26.2 | 0.7 | 0.6 | 2.5 | 0.3 |
| | 50 | 70.7 | 25.5 | 0.6 | 0.5 | 2.4 | 0.3 |
| | 200 | 72.2 | 24.3 | 0.6 | 0.5 | 2.1 | 0.3 |
| | 400 | 73.2 | 23.7 | 0.5 | 0.4 | 2 | 0.2 |
| $A_2$ | 4 | 65.9 | 28.9 | 0.9 | 0.7 | 3.3 | 0.3 |
| | 50 | 67 | 28.1 | 0.8 | 0.7 | 3.1 | 0.3 |
| | 200 | 68.8 | 26.9 | 0.7 | 0.6 | 2.7 | 0.3 |
| | 400 | 69.7 | 26.2 | 0.7 | 0.6 | 2.5 | 0.3 |
| $A_3$ | 4 | 66.9 | 28.2 | 0.8 | 0.7 | 3.1 | 0.3 |
| | 50 | 68 | 27.4 | 0.8 | 0.6 | 2.9 | 0.3 |
| | 200 | 69.7 | 26.2 | 0.7 | 0.6 | 2.5 | 0.3 |
| | 400 | 70.6 | 25.6 | 0.6 | 0.5 | 2.4 | 0.3 |
| $A_4$ | 4 | 68.5 | 27 | 0.8 | 0.6 | 2.8 | 0.3 |
| | 50 | 69.7 | 26.2 | 0.7 | 0.6 | 2.5 | 0.3 |
| | 200 | 71.3 | 25 | 0.6 | 0.5 | 2.3 | 0.3 |
| | 400 | 72 | 24.5 | 0.6 | 0.5 | 2.1 | 0.3 |
| $A_5$ | 4 | 73.3 | 23.6 | 0.6 | 0.4 | 1.9 | 0.2 |
| | 50 | 74.1 | 23 | 0.5 | 0.4 | 1.8 | 0.2 |
| | 200 | 75.7 | 21.8 | 0.4 | 0.4 | 1.5 | 0.2 |
| | 400 | 76.7 | 21 | 0.4 | 0.3 | 1.4 | 0.2 |
| B | 4 | 83.5 | 15.6 | 0.2 | 0.1 | 0.5 | 0.1 |
| | 50 | 90.7 | 9.1 | 0.2 | — | — | — |
| | 200 | 95.7 | 4.2 | 0.1 | — | — | — |
| | 400 | 97 | 3 | — | — | — | — |

These results show the advantage of associating to rhenium a metal from groups III B, IV B and V B: the activity and the stability of such catalysts are better than those of the catalyst which contains only rhenium (catalyst A) or only platinum (catalyst B).

EXAMPLE 3

According to the technique of example 1, there are prepared 9 catalysts C-$C_1$-$C_2$-D-$D_1$-$D_2$-E-$E_1$ and $E_2$, having a neutralization heat by ammonia adsorption of about 7 calories per gram, a specific surface of about 62 m²/g and a pore volume of 54 cc/100 g, and whose composition by weight is as follows:

C: 0.2 % of palladium — 0.2 % of rhenium
$C_1$: 0.2 % of palladium — 0.2% of rhenium-0.2% of germanium
$C_2$: 0.2 % of palladium — 0.2% of rhenium-0.2% of tin
D: 0.2 % of platinum — 0.2% of tungsten
$D_1$: 0.2 % of platinum—0.2% of tungsten- 0.2% of gallium
$D_2$: 0.2% of platinum — 0.2% of tungsten— 0.2% of antimony
E: 0.2% of iridium — 0.2% of molybdenum
$E_1$: 0.2% of iridium—0.2% of molybdenum— 0.2% of thallium
$E_2$: 0.2% of iridium — 0.2% of molybdenum — 0.2% of indium The catalysts C-$C_1$-$C_2$-D-$D_1$-$D_2$ have been reduced at a temperature of 530°C. The catalysts E-$E_1$ and $E_2$ at a temperature of 560°C. These 9 catalysts have been used for dehydrogenating the $C_{10}$-$C_{14}$ cut of example C-D and E form no part of the invention and are only given by way of comparison.

The results are given in table II.

The results obtained in this table II show at first the interest of incorporating a metal from group VIII into the catalyst containing on the one hand, a metal from group VI B or VII B and on the other hand, a metal from groups III A, IV A and V A; the catalysts $C_1$ and $C_2$ (table II) (containing respectively palladium, rhenium and germanium, for the first one, and palladium, rhenium and tin, for the second one), give respectively better results than the catalysts $A_3$ and $A_1$ (table I) containing respectively rhenium and germanium for the first one, rhenium and tin for the second one. The results obtained in this table II also show the superiority of the catalyst containing simultaneously a metal from group VIII, a metal from group VI B or VII B and a metal from groups III A, IV A or V A as compared to the catalysts containing:

either only a metal from group VIII (the results obtained, for example, with the catalysts $C_1$-$C_2$-$D_1$-$D_2$-$E_1$ and $E_2$ may be compared to those obtained with the catalyst B of the table I), or only a metal from group VI B or VII B (the results obtained with the catalysts $C_1$-$C_2$-$D_1$-$D_2$-$E_1$-$E_2$ may be compared, for example, with those obtained with the catalyst A of table I);

or a metal from group VIII and a metal from group VI B or VII B (the results obtained with the catalysts $C_1$-$C_2$-$D_1$-$D_2$-$E_1$ and $E_2$ are to be compared for example with those obtained with the catalysts $C_1$- D and E.

TABLE II

| Catalyst | Catalyst age in hours | n-paraffins | n-mono olefins | iso-olefins + isoparaffins | diolefins | aromatics | % of the charge cracked to $C_1$–$C_5$ hydrocarbons |
|---|---|---|---|---|---|---|---|
|   | 4   | 80   | 18.3 | 0.4 | 0.2 | 0.9 | 0.2 |
| C | 50  | 84.6 | 14.6 | 0.2 | 0.1 | 0.4 | 0.1 |
|   | 200 | 88.3 | 11.5 | 0.1 | —   | 0.1 | —   |
|   | 400 | 89.9 | 10   | 0.1 | —   | —   | —   |
|   | 4   | 56.5 | 35.4 | 1.3 | 1.1 | 5.3 | 0.4 |
| $C_1$ | 50 | 59.6 | 33.2 | 1.2 | 1   | 4.6 | 0.4 |
|   | 200 | 64.6 | 29.8 | 0.9 | 0.8 | 3.5 | 0.4 |
|   | 400 | 66.7 | 28.4 | 0.8 | 0.7 | 3.1 | 0.3 |
|   | 4   | 59.9 | 33   | 1.2 | 1   | 4.5 | 0.4 |
| $C_2$ | 50 | 63.3 | 30.7 | 1   | 0.8 | 3.8 | 0.4 |
|   | 200 | 68.5 | 27   | 0.8 | 0.6 | 2.8 | 0.3 |
|   | 400 | 71.1 | 25.2 | 0.6 | 0.5 | 2.3 | 0.3 |
|   | 4   | 69.5 | 26.3 | 0.7 | 0.6 | 2.6 | 0.3 |
| D | 50  | 74.2 | 22.9 | 0.5 | 0.4 | 1.8 | 0.2 |
|   | 200 | 79.4 | 18.9 | 0.3 | 0.2 | 1   | 0.2 |
|   | 400 | 81.8 | 17   | 0.2 | 0.2 | 0.7 | 0.1 |
|   | 4   | 50.1 | 39.6 | 1.7 | 1.4 | 6.7 | 0.5 |
| $D_1$ | 50 | 53.6 | 37.3 | 1.5 | 1.2 | 5.9 | 0.5 |
|   | 200 | 59   | 33.7 | 1.2 | 1   | 4.7 | 0.4 |
|   | 400 | 60.9 | 32.4 | 1.1 | 0.9 | 4.3 | 0.4 |
|   | 4   | 59.6 | 33.2 | 1.2 | 1   | 4.6 | 0.4 |
| $D_2$ | 50 | 63   | 30.9 | 1   | 0.8 | 3.9 | 0.4 |
|   | 200 | 68.5 | 27   | 0.8 | 0.6 | 2.8 | 0.3 |
|   | 400 | 71.4 | 25   | 0.6 | 0.5 | 2.2 | 0.3 |
|   | 4   | 74.7 | 22.5 | 0.5 | 0.4 | 1.7 | 0.2 |
| E | 50  | 78.7 | 19.4 | 0.3 | 0.3 | 1.1 | 0.2 |
|   | 200 | 83   | 16   | 0.2 | 0.1 | 0.6 | 0.1 |
|   | 400 | 85.6 | 13.8 | 0.1 | 0.1 | 0.3 | 0.1 |
|   | 4   | 66.7 | 27.6 | 0.8 | 0.7 | 2.9 | 0.3 |
| $E_1$ | 50 | 71.2 | 25.1 | 0.6 | 0.5 | 2.3 | 0.3 |
|   | 200 | 76.6 | 21.1 | 0.4 | 0.3 | 1.4 | 0.2 |
|   | 400 | 79.2 | 19.1 | 0.3 | 0.2 | 1   | 0.2 |
|   | 4   | 52.9 | 37.7 | 1.5 | 1.3 | 6.1 | 0.5 |
| $E_2$ | 50 | 56.8 | 35.2 | 1.3 | 1.1 | 5.2 | 0.4 |
|   | 200 | 62.8 | 31   | 1   | 0.9 | 3.9 | 0.4 |
|   | 400 | 66   | 28.8 | 0.9 | 0.7 | 3.3 | 0.3 |

EXAMPLES 4 and 5

These examples are given only by way of comparison and form no part of the present invention.

By using the technique of example 1, a catalyst $D_3$ is prepared, which contains 0.2% by weight of platinum, 0.2 % by weight of tungsten and 0.2 % by weight of gallium.

The carrier of this catalyst consists of eta alumina having a specific surface of 230 m²/g and a total pore volume of 0.57 cc/g (84% of this pore volume corresponding to pores of an average diameter from 50 to 150 A). The neutralization heat of this eta alumina by adsorption of ammonia, was 15 calories per gram. This catalyst has been reduced in a hydrogen stream at a temperature of 530°C. The catalyst had a neutralization heat by ammonia adsorption of 15 calories per gram, its specific surface was 215 m²/g and its pore volume 0.55 cc/g.

By using the technique of example 1, a catalyst $D_4$ is prepared, containing 0.2 % by weight of platinum, 0.2 % by weight of tungsten and 0.2 % by weight of gallium. The carrier of this catalyst consists of a transition alumina whose specific surface is 130 m²/g and whose total pore volume is 0.95 cc/g. The catalyst $D_4$ has been reduced in a hydrogen stream at a temperature of 530°C. The catalyst had a neutralization heat by an ammonia adsorption of 12 calories per gram; its specific surface was 120 m²/g and its pore volume 0.90 cc/g. A $C_{10}$-$C_{14}$ cut, as in example 1, has been passed over these catalysts $D_3$ and $D_4$.

The operating conditions are those mentioned in example 1; the performances of these catalysts $D_3$ and $D_4$ as compared with those of the catalyst $D_1$ of example 6 are shown in table III below.

TABLE III

| Catalyst | Catalyst age in hours | n-paraffins | n-mono olefins | iso-olefins + isoparaffins | diolefins | aromatics | % of the charge cracked to $C_1$–$C_5$ hydrocarbons |
|---|---|---|---|---|---|---|---|
|   | 4   | 50.1 | 39.6 | 1.7 | 1.4 | 6.7  | 0.5 |
| $D_1$ | 50 | 53.6 | 37.3 | 1.5 | 1.2 | 5.9 | 0.5 |
|   | 200 | 59   | 33.7 | 1.2 | 1   | 4.7  | 0.4 |
|   | 400 | 60.9 | 32.4 | 1.1 | 0.9 | 4.3  | 0.4 |
|   | 4   | 31.1 | 41.3 | 4.3 | 3.2 | 19.1 | 1   |
| $D_3$ | 50 | 36.2 | 39.1 | 3.8 | 2.9 | 17.1 | 0.9 |
|   | 200 | 47.3 | 34.3 | 2.7 | 2.1 | 12.8 | 0.8 |
|   | 400 | 50.4 | 32.9 | 2.4 | 1.9 | 11.6 | 0.8 |
|   | 4   | 38.6 | 38.1 | 3.6 | 2.7 | 16.2 | 0.8 |
| $D_4$ | 50 | 43.7 | 35.9 | 3.1 | 2.4 | 14.2 | 0.7 |
|   | 200 | 54.8 | 31.1 | 2.3 | 1.8 | 9.3  | 0.7 |

TABLE III-continued

| Catalyst | Catalyst age in hours | Composition by weight of the liquid product | | | | | % of the charge cracked to $C_1$-$C_5$ hydrocarbons |
|---|---|---|---|---|---|---|---|
| | | n-paraffins | n-mono olefins | iso-olefins + isoparaffins | diolefins | aromatics | |
| | 400 | 57.9 | 29.7 | 1.9 | 1.6 | 8.3 | 0.6 |

These results show the interest of proceeding according to the invention; it is necessary to make use of a carrier of low acidity having a neutralization heat by ammonia adsorption lower than 10 calories per gram, in order to avoid a substantial decrease of the selectivity.

EXAMPLE 6

This example forms no part of the invention.

By making use of the technique of example 1 and of the eta alumina carrier of example 4, there are prepared three catalysts $D_5$-$D_6$ and $D_7$ having the following composition by weight:

$D_5$ : 0.2 % of platinum, 0.2 % of tungsten 0.2 % of gallium, 1 % of lithium $D_6$ : 0.2 % of platinum, 0.2 % of tungsten, 0.2 % of gallium, 1 % of sodium.

$D_7$ : 0.2 % of platinum, 0.2 % of tungsten, 0.2 % of gallium, 1 % of potassium The catalysts $D_5$, $D_6$ and $D_7$ have a neutralization heat by ammonia adsorption of 10 calories per gram, a specific surface of about 215 m²/g and a pore volume of about 0.55 cc/g.

The reduction temperature of these three catalysts was 530°C. The $C_{10}$–$C_{14}$ cut of example 1 was passed over the three catalysts $D_5$, $D_6$ and $D_7$.

The operating conditions are the same as in example 1; the results are given in the following table IV.

TABLE IV

| Catalyst | Catalyst age in hours | Composition by weight of the liquid product | | | | | % of the charge cracked to $C_1$-$C_5$ hydrocarbons |
|---|---|---|---|---|---|---|---|
| | | n-paraffins | n-mono olefins | iso-olefins + isoparaffins | diolefins | aromatics | |
| $D_5$ | 4 | 41.5 | 40.8 | 2.5 | 2.1 | 12.4 | 0.7 |
| | 50 | 45.7 | 38.5 | 2.2 | 1.9 | 11 | 0.7 |
| | 200 | 53.9 | 33.9 | 1.7 | 1.5 | 8.4 | 0.6 |
| | 400 | 56.9 | 32.3 | 1.5 | 1.3 | 7.5 | 0.5 |
| $D_6$ | 4 | 39.4 | 39.7 | 3 | 2.5 | 14.6 | 0.8 |
| | 50 | 44 | 37.5 | 2.6 | 2.2 | 12.9 | 0.8 |
| | 200 | 53.2 | 32.8 | 1.9 | 1.7 | 9.7 | 0.7 |
| | 400 | 56.6 | 31.1 | 1.7 | 1.5 | 8.5 | 0.6 |
| $D_7$ | 4 | 38.8 | 39.2 | 3.1 | 2.7 | 15.3 | 0.9 |
| | 50 | 43.8 | 36.9 | 2.7 | 2.3 | 13.5 | 0.8 |
| | 200 | 53.3 | 32.3 | 1.9 | 1.8 | 10 | 0.7 |
| | 400 | 56.5 | 30.7 | 1.7 | 1.6 | 8.9 | 0.6 |

The acidity of the acid carriers may be considerably decreased by addition of alkaline elements, thereby increasing the selectivity of the catalysts. However, the results are clearly inferior to those obtained with initially non-acid carriers, i.e., the carriers according to the invention.

EXAMPLE 7

This example relates to the dehydrogenation of a steam-cracking gasoline. The feed has the following composition by weight:

- aromatics : 74.4 %
- naphthenes : 16.6 %
- paraffins : 9 %

The main features were as follows:
- bromine number   <0.2
- maleic anhydride index   nil
- potential gumms   nil
- ASTM distillation
    initial point   52°C
    final point   151°C
- total sulfur content   2 ppm by weight This feed is passed, together with hydrogen, through a reactor at an average temperature of 560°C (inlet temperature of 580°C and outlet temperature of 530°C). As catalysts there are used the catalysts A, $A_1$, $A_2$ and $A_3$ of examples 1 and 2, and a catalyst $A_6$ containing 0.2 % of rhenium and 0.2 % of thallium, prepared according to the technique mentioned in example 1, whose neutralization by ammonia adsorption is about 7 calories per gram and having a specific surface of about 62 m²/g and a pore volume of about 54 cc/100 g. The pressure is 15 bars, the hourly feeding rate by volume is two times the catalyst volume and the molecular ratio hydrogen/feed is 5.

The results are given in table V below.

TABLE V

| Catalyst | Composition by weight of the product issued from the reactor | | |
|---|---|---|---|
| | Aromatics | Naphthenes | Paraffins |
| A | 86.7 | 1.8 | 11.5 |
| $A_1$ | 88.1 | 0.7 | 11.2 |
| $A_2$ | 88.5 | 0.2 | 11.3 |
| $A_3$ | 88.2 | 0.4 | 11.4 |
| $A_6$ | 88 | 0.9 | 11.1 |

EXAMPLE 8

There are prepared according to the technique of example 1, four catalysts F-$F_1$G-$G_1$ whose neutralization heat by ammonia adsorption is about 7 calories per gram, having a specific surface of about 62 m²/g and a pore volume of about 54 cc/100 g, and the following composition by weight:

F: 0.2 % of molybdenum
F₁: 0.2 % of molybdenum and 0.2 % of gallium
G: 0.2 % of tungsten
G₁: 0.2 % of tungsten and 0.2 % of germanium The C₁₀– C₁₄ cut of example 1 is passed over these catalysts under the same operating conditions as mentioned in said example 1. The results are given in table VI below.

TABLE VI

| Catalyst | Catalyst age in hours | Composition by weight of the liquid product | | | | | % of the charge cracked to C₁-C₅ hydrocarbons |
|---|---|---|---|---|---|---|---|
| | | n-paraffins | n-mono olefins | iso-olefins + isoparaffins | diolefins | aromatics | |
| F | 4 | 87.1 | 12.3 | 0.3 | 0.1 | 0.1 | 0.1 |
| | 50 | 95.5 | 4.1 | 0.1 | 0.1 | 0.1 | 0.1 |
| | 200 | 98.8 | 1.1 | 0.1 | — | — | — |
| | 400 | 99.4 | 0.6 | — | — | — | — |
| F₁ | 4 | 71.5 | 24.9 | 0.5 | 0.5 | 2.4 | 0.2 |
| | 50 | 74.8 | 22.4 | 0.6 | 0.4 | 1.7 | 0.1 |
| | 200 | 80.5 | 18.1 | 0.2 | 0.1 | 1.0 | 0.1 |
| | 400 | 84.0 | 15.1 | 0.2 | 0.1 | 0.5 | 0.1 |
| G | 4 | 85.6 | 14.0 | 0.2 | 0.1 | 0.4 | 0.1 |
| | 50 | 86.7 | 12.8 | 0.1 | 0.1 | 0.2 | 0.1 |
| | 200 | 89.1 | 10.7 | 0.1 | — | 0.1 | — |
| | 400 | 91.8 | 8.2 | — | — | — | — |
| G₁ | 4 | 68.4 | 27.2 | 0.7 | 0.7 | 2.8 | 0.2 |
| | 50 | 71.8 | 24.6 | 0.6 | 0.5 | 2.2 | 0.3 |
| | 200 | 77.4 | 20.3 | 0.5 | 0.3 | 1.4 | 0.1 |
| | 400 | 80.3 | 18.1 | 0.2 | 0.2 | 1.1 | 0.1 |

What we claim is:

1. In a process comprising dehydrogenating a saturated hydrocarbon containing 3–40 carbon atoms per molecule in contact with a dehydrogenation catalyst, wherein the improvement comprises employing as said dehydrogenation catalyst: (a) alumina, (b) rhenium and (c) at least one metal from groups III A, IV A and V A of the periodic classification of the elements, selected from the group consisting of gallium, indium, thallium, germanium, tin, lead, antimony and bismuth, said catalyst having a specific surface of about 20 to 80 m²/g and a neutralization heat by ammonia adsorption lower than about 10 calories per gram of catalyst at 320°C and under a pressure of 300 mm of mercury, the total content by weight of rhenium being from 0.01 to 1% and the total content by weight of metals from groups III A, IV A and V A being from 0.01 to 0.5%, said catalyst being essentially free of group VIII metals.

2. Aa process according to claim 1, said catalyst having a pore volume from 0.4 to 0.8 cc/g.

3. A process according to claim 1, wherein the alumina is gamma alumina.

4. A process according to claim 1, said catalyst having a total content by weight of rhenium of from 0.1 to 0.5%.

5. A process according to claim 1, wherein said at least one (c) metal is gallium.

6. A process according to claim 1, wherein said at least one (c) metal is indium.

7. A process according to claim 1, wherein said at least one (c) metal is thallium.

8. A process according to claim 1, wherein said at least one (c) metal is germanium.

9. A process according to claim 1, wherein said at least one (c) metal is tin.

10. A process according to claim 1, wherein said at least one (c) metal is lead.

11. A process according to claim 1, wherein said at least one (c) metal is antimony.

12. A process according to claim 1, wherein said at least one (c) metal is bismuth.

13. A process according to claim 1, wherein said saturated hydrocarbon is a naphthenic hydrocarbon.

14. In a process comprising dehydrogenating a saturated hydrocarbon containing 3–40 carbon atoms per molecule in contact with a dehydrogenation catalyst, wherein the improvement comprises employing as said dehydrogenation catalyst: (a) alumina, (b) at least one metal from group VI A or VII A of the periodic classification of elements, selected from the group consisting of molybdenum and tungsten, (c) at least one metal from groups III A, IV A and V A of the periodic classification of the elements, selected from the group consisting of gallium, indium, thallium, germanium, antimony and bismuth, and (d) at least one metal from group VIII selected from the group consisting of platinum, iridium, palladium, ruthenium and rhodium, these catalysts having a specific surface of about 20 to 80 m²/g and a neutralization heat by ammonia adsorption lower than about 10 calories per gram of catalyst at 320°C and under a pressure of 300 mm of mercury, the total content by weight of metals from groups VI B and VII B being from 0.01 to 1%, the total content by weight of metals from groups III A, IV A and V A being from 0.01 to 0.5 and the total content by weight of metals from group VIII being from 0.01 to 1%, said alumina being of insufficient acidity to require the addition of alkaline oxides in order to provide said neutralization heat of lower than about 10 calories per gram.

15. A process according to claim 14, said catalyst having a total content by weight of metals from group VI B, VII B and VIII of from 0.1 to 0.5%.

16. A process according to claim 14, said catalyst having a pore volume of from 0.4 to 0.8 cc/g.

17. A process according to claim 14, wherein the alumina is gamma alumina.

18. A process according to claim 14, wherein said (b) metal is tungsten, said (c) metal is gallium, and said (d) metal is platinum.

19. A process according to claim 14, wherein said (b) metal is tungsten, said (c) metal is antimony, and said (d) metal is platinum.

20. A process according to claim 14, wherein said (b) metal is molybdenum, said (c) metal is thallium, and said (d) metal is iridium.

21. A process according to claim 14, wherein said (b) metal is molybdenum, said (c) metal is indium, and said (d) metal is iridium.

22. A process according to claim 14, wherein said saturated hydrocarbon is a naphthenic hydrocarbon.

23. A process according to claim 1, wherein said dehydrogenation is conducted at 300°–600°C.

24. A process according to claim 13, wherein said dehydrogenation is conducted at 500°–600°C.

25. A process according to claim 14, wherein said dehydrogenation is conducted at 300°–600°C.

26. A process according to claim 14, wherein said dehydrogenation is conducted at 500°–600°C.

* * * * *

UNITED STATES PATENT AND TRADEMARK OFFICE
CERTIFICATE OF CORRECTION

PATENT NO. : 3,980,721

DATED : September 14, 1976

INVENTOR(S) : BERNARD JUGUIN ET AL

It is certified that error appears in the above-identified patent and that said Letters Patent are hereby corrected as shown below:

[73] Assignee: show read --INSTITUT FRANCAIS DU PETROLE--.

Signed and Sealed this

First Day of February 1977

[SEAL]

Attest:

RUTH C. MASON
*Attesting Officer*

C. MARSHALL DANN
*Commissioner of Patents and Trademarks*